(12) United States Patent
DeLucia et al.

(10) Patent No.: US 7,118,639 B2
(45) Date of Patent: Oct. 10, 2006

(54) STRUCTURED MATERIAL HAVING APERTURES AND METHOD OF PRODUCING THE SAME

(75) Inventors: Mary Lucille DeLucia, Roswell, GA (US); Sandy Chi-Ching Tan, Roswell, GA (US); Eugenio Go Varona, Marietta, GA (US); Jessica B. King, Roswell, GA (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 0 days.

(21) Appl. No.: 09/871,171

(22) Filed: May 31, 2001

(65) Prior Publication Data
US 2003/0056893 A1    Mar. 27, 2003

(51) Int. Cl.
*B32B 31/26* (2006.01)

(52) U.S. Cl. .................. 156/85; 156/183; 156/244.11; 156/253

(58) Field of Classification Search ............. 156/85, 156/183, 250, 256, 259, 244.11, 253, 84, 156/167; 604/358, 365, 366, 367, 378, 385.01, 604/385.23; 428/136, 131, 134; 442/394, 442/400, 401, 361, 362
See application file for complete search history.

(56) References Cited

U.S. PATENT DOCUMENTS

| | | | |
|---|---|---|---|
| 3,331,728 A * | 7/1967 | Lane | 161/112 |
| 3,338,992 A | 8/1967 | Kinney | |
| 3,341,394 A | 9/1967 | Kinney | |
| 3,502,763 A | 3/1970 | Hartmann | |
| 3,542,615 A | 11/1970 | Dobo et al. | |
| 3,622,434 A * | 11/1971 | Newman | 428/179 |
| 3,692,618 A | 9/1972 | Dorschner et al. | |
| 3,802,817 A | 4/1974 | Matsuki et al. | |
| 3,849,241 A | 11/1974 | Butin et al. | |
| 4,340,563 A | 7/1982 | Appel et al. | |
| 4,560,372 A | 12/1985 | Pieniak | |
| 4,762,521 A | 8/1988 | Roessler et al. | |
| 4,842,596 A | 6/1989 | Kielpikowski et al. | |
| 5,032,121 A * | 7/1991 | Mokry | 604/385.26 |
| 5,057,368 A | 10/1991 | Largman et al. | |
| 5,069,970 A | 12/1991 | Largman et al. | |
| 5,108,820 A | 4/1992 | Kaneko et al. | |
| 5,108,827 A | 4/1992 | Gessner | |
| 5,171,239 A | 12/1992 | Igaue et al. | |
| 5,207,664 A | 5/1993 | Blanco | |

(Continued)

FOREIGN PATENT DOCUMENTS

DE          2223780      * 11/1973

(Continued)

OTHER PUBLICATIONS

A.A. Burgeni and C. Kapur, *Capillary Sorption Equilibria in Fiber Masses*, Textile Research Journal, vol. 37, May 1967, pp. 356-366.

*Primary Examiner*—Jessica Rossi
(74) *Attorney, Agent, or Firm*—Pauley Peterson & Erickson

(57) ABSTRACT

A method for producing an apertured structured material for accommodating passage of fluids, particularly high viscosity fluids, through the apertured structured material. In one embodiment, the apertured structured material is a composite material formed by differential shrinkage of a shrinkable second layer, for example an ethylene-propylene copolymer, which is laminated to a first layer, for example a polypropylene polymer. During the differential shrinkage process, a plurality of slits which are formed in the second layer open to form uniformly-shaped apertures. In another embodiment, an apertured structured heterogenous material is made of a heterogeneous mixture of at least two homogeneous fiber sets or components having different shrinkage extents.

14 Claims, 8 Drawing Sheets

U.S. PATENT DOCUMENTS

| | | | |
|---|---|---|---|
| 5,257,982 A | 11/1993 | Cohen et al. | |
| 5,272,236 A | 12/1993 | Lai et al. | |
| 5,277,976 A | 1/1994 | Hogle et al. | |
| 5,294,482 A | 3/1994 | Gessner | |
| 5,322,728 A | 6/1994 | Davey et al. | |
| 5,336,552 A | 8/1994 | Strack et al. | |
| 5,376,198 A * | 12/1994 | Fahrenkrug et al. | 156/164 |
| 5,422,172 A * | 6/1995 | Wu | 442/62 |
| 5,466,410 A | 11/1995 | Hills | |
| 5,482,772 A | 1/1996 | Strack et al. | |
| 5,514,470 A * | 5/1996 | Haffner et al. | 428/343 |
| 5,567,501 A | 10/1996 | Srinivasan et al. | |
| 5,571,619 A | 11/1996 | McAlpin et al. | |
| 5,674,211 A * | 10/1997 | Ekdahl | 604/383 |
| 5,679,042 A | 10/1997 | Varona | |
| 5,700,255 A * | 12/1997 | Curro et al. | 604/385.3 |
| 5,789,328 A * | 8/1998 | Kurihara et al. | 442/387 |
| 5,814,178 A * | 9/1998 | Jacobs | 156/290 |
| 5,830,555 A | 11/1998 | Srinivasan et al. | |
| 5,851,935 A | 12/1998 | Srinivasan et al. | |
| 5,914,184 A | 6/1999 | Morman | |
| 5,990,377 A | 11/1999 | Chen et al. | |
| 6,001,303 A | 12/1999 | Haynes et al. | |
| 6,491,777 B1 * | 12/2002 | Bevins et al. | 156/167 |
| 6,503,431 B1 * | 1/2003 | Kasai et al. | 264/171.13 |
| 6,803,334 B1 * | 10/2004 | Mizutani et al. | 442/394 |
| 2002/0028624 A1 * | 3/2002 | Mizutani et al. | 442/394 |

FOREIGN PATENT DOCUMENTS

| | | | |
|---|---|---|---|
| DE | 19523497 | * | 1/1997 |
| EP | 0 687 757 A2 | | 12/1995 |
| EP | 0 586 924 | | 10/1997 |
| GB | 1 293 456 | | 10/1972 |
| GB | 2 284 786 A | | 6/1995 |
| JP | 8-176947 | | 7/1996 |
| WO | WO 00/38918 | * | 7/2000 |

* cited by examiner

STRUCTURED MATERIAL HAVING APERTURES AND METHOD OF PRODUCING THE SAME

BACKGROUND OF THE INVENTION

1. Field of the Invention

This invention relates to a method for producing an apertured structured material, for example a cover material or topsheet for personal care absorbent articles including diapers, feminine pads, incontinence garments, training pants, wound care products, and the like. The apertured structured material according to this invention provides a structure for accommodating passage of fluids, particularly high viscosity fluids such as menses, runny bowel movements, wound exudate and blood, therethrough.

2. Description of Related Art

Personal care absorbent articles such as sanitary napkins, disposable diapers, incontinent-care pads and the like are widely used, and much effort has been made to improve the effectiveness and functionalities of these articles. Conventional cover materials used in personal care absorbent articles do not provide for high viscosity fluids, for example menses, runny bowel movements, wound exudate and blood. As a result, the conventional cover materials used in personal care absorbent articles leak and contribute to poor skin health. Many conventional liners absorb water from the high viscosity fluids. However, these conventional liners do not provide for particle intake. As a result, the particles contained within the high viscosity fluids separate during absorption of the water and tend to remain on the surface of the liner to produce undesired interactions with the wearer's skin.

Many conventional intake liners used in personal care absorbent articles such as feminine pads and diaper products require holes to provide appropriate performance. Two valuable properties for good performance are intake rate and rewet value. Currently, there are several model materials which provide adequate performance. However, these materials are costly to manufacture.

Accordingly, there is a need for a method or process for providing an improved structured material which effectively manages high viscosity fluids such as menses, runny bowel movements, wound exudates and blood.

There is also a need for a method or process for producing a cost-effective apertured structured material having intake and rewet properties at parity with or superior to more expensive model cover materials.

SUMMARY OF THE INVENTION

Materials suitable as a cover material or intake liner for feminine care products must quickly and efficiently handle menses. Menses has an average viscosity of approximately 10 cP. This is a slightly higher viscosity than the viscosity of water, which is about 1.0 cP. The suitable cover material should have a fast intake rate for high viscosity fluids, prevent menses from flowing back to the surface (reduce rewet), and allow only minimal staining. An ideal cover material may have the performance of a film (clean and dry) with the clothlike feel of spunbond.

Materials suitable for use as a cover material or intake liner for infant care, including diapers and training pants, must quickly and efficiently handle runny bowel movements without compromising the management of other fluids such as urine. A runny bowel movement has an average viscosity of about 25 Poise and a range of about 0.1 Poise to about 110 Poise. Approximately 87% of a runny bowel movement is water and the remaining 13% is composed of particles. The particles range in size from about 5.0 microns to about 900 microns with an average size of about 100 microns. Desirably, the cover material has a pore radius of greater than about 200 microns, more desirably greater than about 600 microns, to pass bowel movement particles through the cover material. It is also desirable to enhance pore size and pore volume to increase web permeability, thereby increasing the fluid intake rate. The cover material should also have a single point acquisition (direct intake and localization of runny bowel movements), high z-directional flow, rapid dewatering, and surface flow resistance.

The high viscosity fluid needs for professional health care, including bandages and the like, are slightly different than those for feminine care and infant care. The main priority for the development of fenestration products is to produce cost-effective alternatives for the current foam pads. The fenestration products should have a cover material with a high coefficient of friction to prevent the surgical tools from slipping on the fenestration reinforcement, and an ability to absorb wound exudates and other surgical fluids.

Accordingly, it is one object of this invention to provide a process for making an apertured structured material for use as a cover material in a personal care absorbent article for managing high viscosity fluids, for example menses, runny bowel movements, wound exudates and blood, without compromising the management of other fluids, for example urine.

It is another object of this invention to provide a process for making an apertured structured material for a personal care absorbent article which is soft and comfortable, absorbent, clean and dry.

It is another object of this invention to provide a process for producing an apertured structured material which has fluid intake and rewet properties similar to or better than more expensive model materials.

These and other objects of this invention are addressed by providing a continuous process for producing an apertured structured material suitable for use in a personal care absorbent article for managing high viscosity fluids. The apertured structured material may be a composite material having at least two layers with unique polymer composition or a heterogenous material having a heterogeneous mixture of at least two different fiber sets, each with a unique polymer composition.

Desirably, the second layer or fiber set is made from a polymer or polymer blend different from the polymer or polymer blend of the first layer or fiber set to promote differential shrinkage of the layers or fiber sets. Thus, the second layer or fiber set has a shrinkage extent, at constant temperature, different than the shrinkage extent of the first layer or fiber set. The polymers selected for the second layer or fiber set and the polymers selected for the first layer or fiber set have sufficiently different propensities to shrink over a range of temperatures, and desirably, have different orientation, crystallization, solidification and/or elastic properties. In one embodiment of this invention, a similar polymer or polymer blend is selected for the first layer or fiber set and the second layer or fiber set, having a different crystallization and/or fiber orientation to produce different shrinkage extents.

The structured material is produced or formed by a differential shrinkage process. The shrinkable second layer or fiber set is made of a polymer or polymer blend which may or may not have a shrinking point lower than the shrinking point of the polymer or polymer blend of the first layer or fiber set. For example, the second layer or fiber set is made of an ethylene-propylene copolymer and the first layer or fiber set is made of a propylene polymer. The material is heated to a temperature corresponding to at least the shrinking point of the second layer or fiber set, causing the second layer or fiber set to shrink. This shrinkage of the second layer or fiber set results in bunching or puckering of the first layer or fiber set, thus forming or creating the structure. Because this differential shrinkage may be a latent process, the differential shrinkage process may be induced during the fabrication of the structured material or it may be delayed until the structured material is transferred to a converting machine or product manufacturing site. It is apparent to those having ordinary skill in the art that the polymer or polymer blend used to produce the first layer or fiber set and the second layer or fiber set may be exploited so that the first layer or fiber set will shrink relative to the second layer or fiber set.

In one embodiment of this invention, the material may be slit apertured before the differential shrinkage process. For example, the composite material is passed through a slitting device having a plurality of slitting knives which cut or form slits in the second layer. Each slit expands or opens to form a corresponding aperture when the composite material is heated.

The structured material produced according to this invention is particularly useful as a cover material for management of high viscosity fluids, for example menses, runny bowel movement, wound exudate and blood, and may be used as an intake liner and/or a cost-effective replacement for surge materials. The structured material exhibits fluid intake rates and low rewet values similar to or better than more expensive model cover materials.

DEFINITIONS

As used herein, the term "film" refers to a thermoplastic film made using a film extrusion and/or forming process, such as a cast film or blown film extrusion process.

As used herein, the term "nonwoven fabric or web" means a web having a structure of individual fibers or threads which are interlaid, but not in an identifiable manner, as in a knitted fabric. Nonwoven fabrics or webs have been formed from many processes such as, for example, meltblowing processes, spunbonding processes, and bonded carded web processes. The basis weight of nonwoven fabrics is usually expressed in ounces of material per square yard (osy) or grams per square meter (gsm) and the fiber diameters are usually expressed in microns. (Note that to convert from osy to gsm, multiply osy by 33.91).

As used herein, the term "spunbond fibers" refers to small diameter fibers which are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., U.S. Pat. No. 3,692,618 to Dorschner et al., U.S. Pat. No. 3,802,817 to Matsuki et al., U.S. Pat. No. 3,338,992 and U.S. Pat. No. 3,341,394 to Kinney, U.S. Pat. No. 3,502,763 to Hartmann, and U.S. Pat. No. 3,542,615 to Dobo et al. Spunbond fibers are generally not tacky when they are deposited onto a collecting surface. Spunbond fibers are generally continuous and have average diameters (from a sample of at least 10) larger than 7 microns, more particularly, between about 10 and 20 microns. The fibers may also have shapes such as those described in U.S. Pat. No. 5,277,976 to Hogle et al., U.S. Pat. No. 5,466,410 to Hills, and U.S. Pat. No. 5,069,970 and U.S. Pat. No. 5,057,368 to Largman et al., which describe hybrids with unconventional shapes.

The term "meltblown fibers" means fibers formed by extruding a molten thermoplastic material through a plurality of fine, usually circular, die capillaries as molten threads or filaments into converging high velocity gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin and in U.S. Pat. No. 6,001,303 to Haynes, et al. Meltblown fibers are microfibers which may be continuous or discontinuous, are generally smaller than 10 microns in diameter, and are generally self bonding when deposited onto a collecting surface. Meltblown fibers used in the present invention are preferably substantially continuous in length.

As used herein, the term "polymer" generally includes, but is not limited to, homopolymers, copolymers, such as for example, block, graft, random and alternating copolymers, terpolymers, etc., and blends and modifications thereof. Further, unless otherwise specifically limited, the term "polymer" shall include all possible geometric configurations of the molecule. These configurations include, but are not limited to, isotactic, syndiotactic and random symmetries.

As used herein, the term "bicomponent fibers" refers to fibers which have been formed from at least two polymers extruded from separate extruders but spun together to form one fiber. The polymers are arranged in substantially constantly positioned distinct zones across the cross-section of the bicomponent fibers and extend continuously along the length of the bicomponent fibers. The configuration of such a bicomponent fiber may be, for example, a sheath/core arrangement wherein one polymer is surrounded by another or may be a side-by-side arrangement or an "islands-in-the-sea" arrangement. Bicomponent fibers are taught in U.S. Pat. No. 5,108,820 to Kaneko et al., U.S. Pat. No. 5,336,552 to Strack et al., and European Patent 0586924. For two component fibers, the polymers may be present in ratios of 75/25, 50/50, 25/75 or any other desired ratios.

As used herein, the term "biconstituent fibers" refers to fibers which have been formed from at least two polymers extruded from the same extruder as a blend. Biconstituent fibers do not have the various polymer components arranged in relatively constantly positioned distinct zones across the cross-sectional area of the fiber and the various polymers are usually not continuous along the entire length of the fiber, but rather typically form fibrils or protofibrils which start and end at random. Biconstituent fibers are sometimes also referred to as multiconstituent fibers. Fibers of this general type are taught, for example, by U.S. Pat. Nos. 5,108,827 and 5,294,482 to Gessner.

As used herein, the term "bonded carded web" refers to webs made from staple fibers which are sent through a combing or carding unit, which breaks apart and aligns the staple fibers in the machine direction to form a generally machine direction-oriented fibrous nonwoven web. Such fibers are usually purchased in bales which are placed in a picker which separates the fibers prior to the carding unit. Once the web is formed, it is then bonded by one or more of several known bonding methods. One such bonding method is powder bonding, wherein a powdered adhesive is distributed through the web and then activated, usually by heating the web and adhesive with hot air. Another suitable bonding method is pattern bonding, wherein heated calender rolls or ultrasonic bonding equipment are used to bond the fibers together, usually in a localized bond pattern, though the web can be bonded across its entire surface, if so desired. Another suitable and well-known bonding method, particularly when using bicomponent staple fibers, is through-air bonding.

As used herein, the term "composite" or "composite material" refers to a material which is comprised of one or more layers of nonwoven fabric combined with one or more other fabric or film layers. The layers are usually selected for the different properties they will impart to the overall composite. The layers of such composite materials are usually secured together through the use of adhesives, entanglement or bonding with heat and/or pressure.

As used herein, the term "personal care product" or "personal care absorbent product" means feminine hygiene products, diapers, training pants, absorbent underpants, adult incontinence products, wipes, wound care products, including bandages, fenestration products and the like.

As used herein, the term "shrinkage extent" refers to an amount of shrinkage of a fiber or a component when the fiber or component is activated to shrink, for example by applying or introducing heat to the fiber or component at a temperature greater than a shrinking temperature of the fiber or component or at least one of the fiber or components, if the fiber or a material comprises more than one component.

Fiber shrinkage extent and "percent shrinkage" may be measured using a simple test wherein fibers are extruded at several different draw pressures, for example at 0 psi, 7 psi and 14 psi. The extruded fibers are placed in an oven set at a constant temperature for a given period of time. For example, the fibers in accordance with this invention where placed in a Thermolyne 9000 oven set at a constant temperature of about 135° C. for a five minute period. The length of each fiber is measured before it is placed in the oven and after it has been heated in the oven for the given period of time. The fiber shrinkage extent or extent of shrinkage can be determined by subtracting the final fiber length from the initial fiber length. The percent shrinkage can be determined by subtracting the final fiber length from the initial fiber length, dividing by the initial fiber length and multiplying by 100. Referring to the above example, a fiber having an initial length of 10 inches and a final length of 8.0 inches will have a percent shrinkage of 20%.

$$\frac{(10.0 - 8.0)}{10.0} \times 100 = 20\% \qquad \text{Eq. (1)}$$

The percent shrinkage may be from about 0% to about 99%, depending upon fiber composition, fiber denier, and process conditions.

As used herein, the term "thermoplastic" describes a material that softens when exposed to heat and which substantially returns to a nonsoftened condition when cooled to room temperature.

As used herein, the term "z-direction" refers to fibers disposed outside of the plane of orientation of a web, such fibers having a z-direction component resulting from post-forming processing of a nonwoven web, such as differential shrinkage and/or creping the nonwoven web.

As used herein, the term "homogeneous component" refers to a component having uniform composition or structure.

"Friction" refers to a force that resists relative motion between two bodies in contact. The term "coefficient of friction" refers to the ratio of the magnitude of the force of friction to the magnitude of the normal force applied to an object being moved along a surface. An increased coefficient of friction enables two bodies to stay in contact more easily than a lower coefficient of friction, thus, it is more difficult to separate two bodies having an increased coefficient of friction than it is to separate two bodies having a lower coefficient of friction.

"Peel force" refers to a force that tends to pull two adjoining bodies away from one another in opposite directions generally perpendicular to a plane in which the bodies are joined.

"Topography" refers to the surface features of an object, including height and texture.

These terms may be defined with additional language in the remaining portions of the specification.

DETAILED DESCRIPTION

Figure 1:
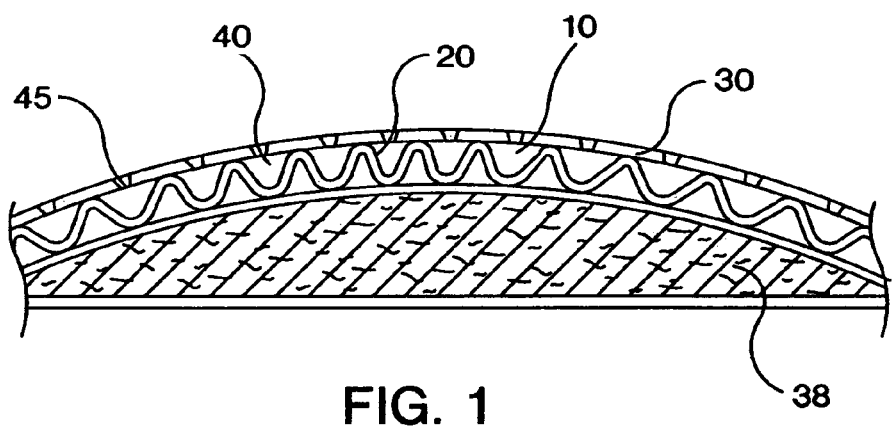
FIG. 1 is a perspective view of an exemplary apertured structured composite material produced in accordance with one embodiment of this invention.

This invention relates to an apertured structured material 10, for example a cover material or topsheet for use in a personal care absorbent article as shown in FIG. 1, which when utilized with an absorbent core 38, permits superior management of high viscosity fluids. Proper management of these high viscosity fluids for feminine care in particular requires good intake (absorbency), low staining (cleanliness), low rewet and low fluid retention (dryness).

Accordingly, this invention provides a continuous process or method for producing a structured material 10 having apertures 45 if desired. The structured material 10 produced in accordance with this invention has high permeability, significant fiber orientation in the z-direction (bulk) and tactile properties for enhanced dryness.

In accordance with one embodiment of this invention, the continuous process produces a structured composite material 10 having a second layer 30, for example a film liner, applied and/or bonded to a first layer 20, for example a substrate. The second layer 30 subsequently shrinks relative to the first layer 20 to produce a structure 40 of the composite material. Such shrinkage is referred to as "differential shrinkage." In accordance with one embodiment of this invention, the first layer 20 may shrink relative to the second layer 30, depending on the polymer or polymer blend chosen to form the first layer or component and the second layer or component. Further, in accordance with one embodiment of this invention during the differential shrinkage process a plurality of slits 44 formed in the second layer 30 each open to form an aperture 45.

The process for producing the structured composite material 10 begins with forming the first layer 20. The first layer 20 may comprise more than one layer. The first layer 20 is formed or produced by any conventional means well known in the art. Desirably, the first layer 20 has an initial basis weight of about 0.2 osy to about 2.0 osy, more desirably about 0.3 osy to about 1.5 osy. The combined initial basis weight of the first layer 20 and the second layer 30 should be lower than the desired basis weight of the final product. The first layer 20 may be pleated, corrugated, thermoformed or embossed and desirably has a high modulus and high resiliency to maintain its structure during packaging and use.

Desirably, a fibrous nonwoven web is used as a base material from which the first layer 20 is formed. The nonwoven web may be any type of thermoplastic nonwoven web. For instance, the nonwoven web may be a spunbond web, a meltblown web, a bonded carded web, or a combination including any of the above. Suitable base materials include spunbond-meltblown-spunbond laminates, coform, spunbond-film-spunbond laminates, bicomponent spunbond, bicomponent meltblown, biconstituent spunbond, biconstituent meltblown, pulp, superabsorbent, and combinations thereof.

A wide variety of thermoplastic polymer materials can be used to make the nonwoven web. Exemplary polymer materials include without limitation, polypropylene, polyethylene (high and low density), ethylene copolymers with $C_3$–$C_{20}$ α-olefins, propylene copolymers with ethylene or $C_4$–$C_{20}$ α-olefins, butene copolymers with ethylene, propylene, or $C_5$–$C_{20}$ α-olefins, polyvinyl chloride, polyesters, polyamides, polyfluorocarbons, polyurethane, polystyrene, polyvinyl alcohol, caprolactams, and cellulosic and acrylic resins. Bicomponent and biconstituent thermoplastic webs may also be utilized, as well as webs containing blends of one or more of the above-listed thermoplastic polymers.

Suitable polyolefins include, but are not limited to, polyethylene, polypropylene, polybutylene, and the like; suitable polyamides include, but are not limited to, nylon 6, nylon 6/6, nylon 10, nylon 12 and the like; and suitable polyesters include, but are not limited to, polyethylene terephthalate, polybutylene terephthalate and the like. Particularly suitable polymers for use in the present invention are polyolefins including polyethylene, for example, linear low density polyethylene, low density polyethylene, medium density polyethylene, high density polyethylene and blends thereof; polypropylene; polybutylene and copolymers as well as blends thereof. Additionally, the suitable fiber forming polymers may have thermoplastic elastomers blended therein. In addition, staple fibers may be employed in the nonwoven web as a binder.

After the first layer 20 is formed, a second layer 30, desirably a shrinkable film or web liner, is formed and applied, laminated or bonded to the first layer 20 to form a composite material. The second layer 30 may comprise one layer or more than one layer. The second layer 30 is desirably compliant, soft feeling, and non-irritating to a wearer's skin. Further, the second layer 30 can be less hydrophilic than the absorbent core 38 to present a relatively dry surface to the wearer and permit liquid to readily penetrate through its thickness. Desirably, the second layer 30 has a basis weight of about 0.3 osy to about 2.5 osy, more particularly about 0.44 osy to about 1.0 osy.

The second layer 30 may be placed or applied onto the first layer 20 by an appropriate technology considering the materials used to form the first layer 20 and the second layer 30. For example, the second layer 30 may be extruded or sprayed onto the first layer 20 in a desired pattern. For a smocked effect, parallel lines are appropriate. A variety of shapes and/or patterns other than parallel lines may be used.

Desirably, the second layer 30 is laminated or bonded to the first layer 20 by using thermal bonding, adhesive bonding including pin bonding, differential speed bonding and/or other bonding techniques well known in the art. Thermal point bonding and adhesive spiral bonding are desired because these bonding methods do not damage the first layer 20. In one embodiment of this invention, a plurality of apertures 45 are formed or created in the second layer 30 during the thermal bonding process. The apertures 45 can be formed by several conventional methods, including, but not limited to, die cutting, pin embossing, laser embossing and thermal embossing and result from the shrinking of the second layer 20 at bond points during the bonding process. The aperture size, depth and cross-sectional area are dependent on the bond pattern used, the bond area, the bonding temperature and the degree of stretching of the second layer 30 prior to the bonding process.

The apertured structured material 10 in accordance with this embodiment can be incorporated into a personal care absorbent article suitable for runny bowel movement separation and containment and menses management and containment. At least a portion of the second layer 30 includes the apertures 45 which extend through the second layer 30 to permit passage of high viscosity fluids through the second layer 30. Desirably, the structure 40 produced during the differential shrinkage process discussed below, forms a frusto-conical shape around each aperture 45 to direct fluid flow through the second layer 30, thus preventing rewet or fluid flow back through the second layer 30.

The apertures 45 may have a diameter of about 100 microns to about 10,000 microns. In one embodiment of this invention wherein the apertures are not circular, the term "diameter" refers to a width of the apertures 45 sufficiently large to allow transfer therethrough of particles having a width of about 100 microns to about 10,000 microns. Desirably, the apertures 45 are formed in the second layer 30 so that the second layer 30 is effective in transferring particles into the structure 40 and the first layer 20 is effective in retaining them. In accordance with one embodiment of this invention, the apertures may be formed in the first layer 20 as well as in the second layer 30. The size and/or direction of the apertures 45 can be controlled through the application of heat during the aperture forming process.

Desirably, the second layer 30 is made of a polymer or polymer blend different from the polymer or polymer blend of the first layer 20 to promote the differential shrinkage of layers 20, 30, as discussed below. Thus, the second layer 30 has a shrinkage extent, at constant temperature, different than the shrinkage extent of the first layer 20. In one embodiment of this invention, the polymers selected for the second layer 30 and the polymers selected for the first layer 20 have sufficiently different shrinking points, desirably having a shrinking point difference of at least about 10° C., and, desirably, have different orientation, crystallization, solidification and/or elastic properties. The shrinking point difference between the selected polymers facilitates the heat activated bonding process.

In one embodiment of this invention, the same or similar polymer is selected for the first layer 20 and the second layer 30, having a different crystallization and/or orientation to produce different shrinkage extents for the first layer 20 and the second layer 30. Further, the polymer or polymer blend may be treated, for example with additives and/or fillers to produce different shrinkage extents.

The second layer 30 desirably is a film formed from any suitable film-forming thermoplastic polymer. Examples of suitable polymers include without limitation polyethylene, polypropylene, copolymers of mainly ethylene and $C_3$–$C_{12}$ alpha-olefins (commonly known as linear low density polyethylene), copolymers of mainly propylene with ethylene and/or $C_4$–$C_{12}$ alpha-olefins, and flexible polyolefins including propylene-based polymers having both atactic and isotactic propylene groups in the main polypropylene chain. Other suitable polymers include without limitation elastomers, for example polyurethanes, copolyether esters, polyamide polyether block copolymers, ethylene vinyl acetate copolymers, block copolymers having the general formula A-B-A' or A-B such as copoly (styrene/ethylene-butylene), styrene-poly (ethylene-propylene)-styrene, styrene-poly (ethylene-butylene)-styrene, polystyrene/poly (ethylene-butylene)/polystyrene, poly (styrene/ethylene-butylene/styrene), and the like. Metallocene-catalyzed polyolefins are also useful, including those described in U.S. Pat. Nos. 5,571,619; 5,322,728; and 5,272,236, the disclosures of which are incorporated herein by reference.

A filler, for example calcium carbonate, diatomaceous earth, titanium dioxide, talc, or the like, may be added to the film to provide a pleasing hand to the second layer 30. The filler enhances the heat absorption properties of the polymers and thus increases the options for thermal initiation of shrinkage.

One advantage of using a film as the second layer 30 is its surface cleanliness after insult. Film materials generally resist fluid penetrations on the surface except for open areas such as apertures. Thus, the film provides a masking effect for fluids such as menses and runny bowl movements. It is also desirable to provide a film with topography such that it resists back flow of the fluid to the surface while under pressure. Thus, it is desirable to use a film which has an open structure or apertures and a polymer formulation which enhances the bunching or puckering effects of the composite material 10 during differential shrinkage.

Alternatively, the second layer 30 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. If the second layer 30 is not apertured, it should be formed from an open structure material, such as a nonwoven web having openings of about 100 microns to about 10,000 microns (large enough to accommodate particles of similar or smaller size) between the fibers.

Various woven and nonwoven fabrics can be used for the second layer 30. For example, the second layer 30 can be composed of a meltblown or spunbond web of polyolefin fibers. The second layer 30 can also be a bonded carded web composed of natural and/or synthetic fibers. The second layer 30 can be composed of a substantially hydrophobic material, and the hydrophobic material can, optionally, be treated with a surfactant or otherwise processed to impart a desired level of wettability and hydrophilicity. For example, the material can be surface treated with about 0.10 weight percent to about 0.50 weight percent, more desirably about 0.20 weight percent to about 0.40 weight percent of a surfactant commercially available from the Cognis Corp. Of Ambler, Pa. and produced in Cincinnati, Ohio under the trade designation GLUCOPON. Other suitable surfactants can also be used. The surfactant can be applied by any conventional means, such as spraying, printing, brush coating or the like. The surfactant can be applied to the entire second layer 30 or can be selectively applied to particular sections of the second layer 30, such as a medial section along a longitudinal centerline.

During or after the fabrication process, other optional steps may be included for completeness. For example, post fabrication treatments including surface treatments and UV and/or microwave treatments may be included as steps in the process of producing the structured composite material 10 according to this invention.

In one embodiment of this invention, the second layer 30 is stretched in a machine direction before it is bonded to the first layer 20. The second layer 30 is pre-oriented using a machine direction orienter prior to bonding the second layer 30 to the first layer 20. Desirably, the second layer 30 is stretched from about 1.5 times to about 6.0 times its initial length, more desirably about 2.0 to about 4.0 times its initial length, still more desirably about 3.0 times its initial length. The second layer 30 may be stretched prior to bonding to the first layer 20 using any conventional stretching means known in the art.

After the second layer 30 is bonded, laminated or applied to the first layer 20, the structure 40 of the composite material is produced. The structure 40, defined by the first layer 20 and the second layer 30, is produced or formed by differential shrinkage of the layers 20, 30. For example, the shrinkable second layer 30 is made of a polymer or polymer blend such as an ethylene-propylene copolymer, having a shrinking point lower than the shrinking point of the polymer or polymer blend of the first layer 20, such as a polypropylene polymer. The composite material is heated to a temperature corresponding to at least the shrinking point of the second layer 30, whereby shrinking the second layer 30. Desirably, the composite material is heated to a temperature below the shrinking point of the first layer 20. In accordance with one embodiment of this invention, the first layer 20 may shrink, however to a lesser extent than the second layer 30.

This differential shrinkage of the second layer 30 results in bunching or puckering of the first layer 20 and the second layer 30, thus forming or creating the structure 40 defined by the first layer 20 and the second layer 30. Because this differential shrinkage may be a latent process, the differential shrinkage may be induced during the fabrication of the structured composite material 10 or it may be delayed until the structured composite material 10 is transferred to a converting machine or product manufacturing site. Advantages to being able to produce the structure 40 at any time during the fabrication process include the ability to transport and handle a relatively flat composite material and the increased integrity of the structure 40, i.e. the structure 40 will not be damaged during transportation to the manufacturing site.

Figure 2:
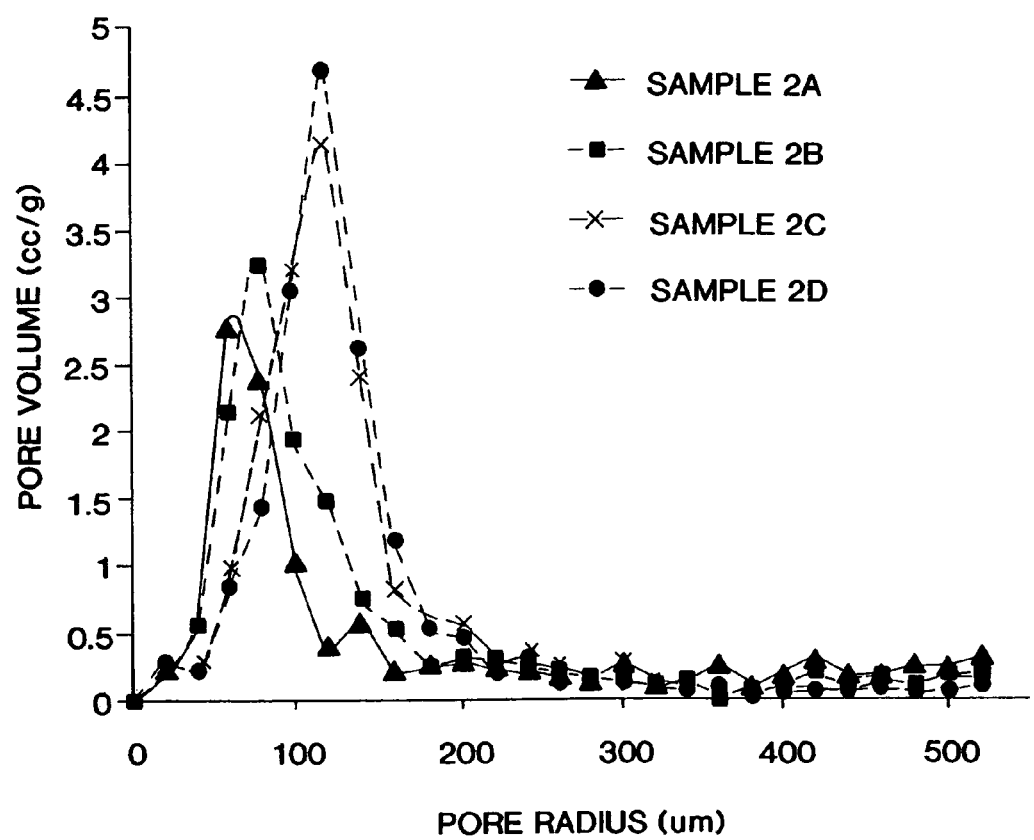
FIG. 2 is a pore radius distribution chart for a structured material produced in accordance with one embodiment of this invention.

The polymers or the polymer blends used to produce the first layer 20 and the second layer 30 can be chosen to exploit the differential shrinkage anticipated by the polymer properties. It is apparent to those having ordinary skill in the art that the polymer or polymer blend used to form the first layer 20 and the second layer 30 may be exploited to produce the first layer 20 which shrinks relative to the second layer 30. The structured composite material 10 produced by differential shrinkage of the fibers changes in density and porosity in response to the temperature profile during heat shrinkage. As shown in FIG. 2, differential shrinkage of the layers 20, 30 provides an increase in overall pore radius and pore volume to the structured composite material 10, which increases the bulk and decreases the overall density of the structured composite material 10. FIG. 2 is a pore radius distribution chart the data for which was obtained as discussed below in TEST METHODS. Samples of a structured composite material 10 made of a bilayer spunbond web having the first layer 20 made of a polypropylene polymer and the second layer 30 made of an ethylene-propylene random copolymer (3% by weight ethylene and 97% by weight propylene) were passed through a cure oven at a temperature between about 270° F. and about 290° F. at a rate of about 50 feet per minute (fpm) to about 250 fpm.

Figure 3:
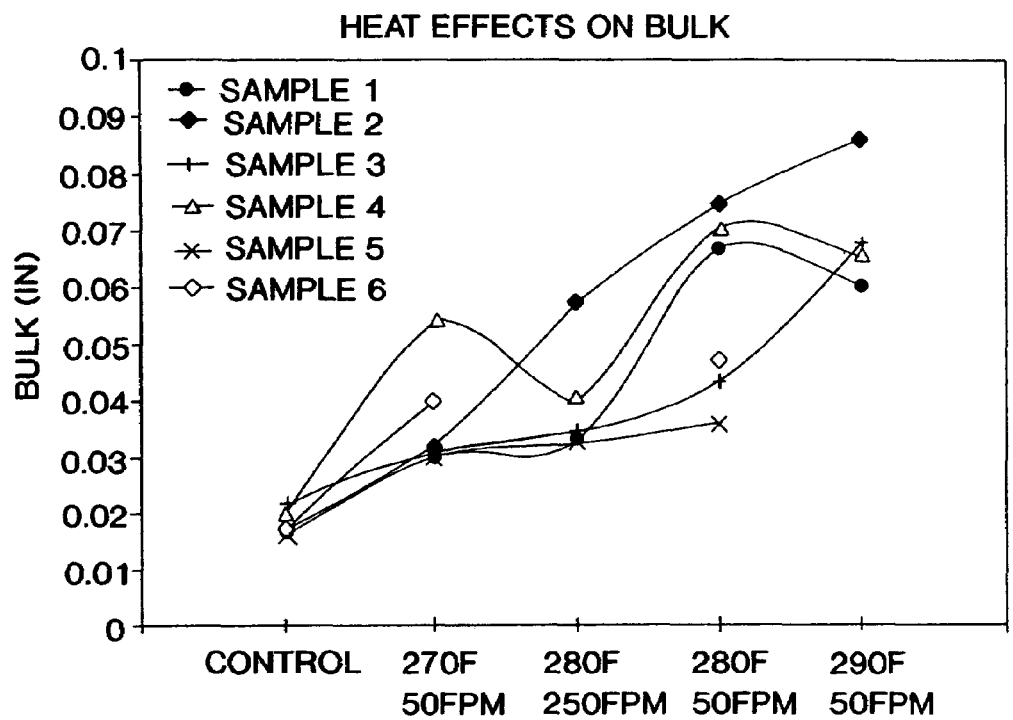
FIG. 3 shows the effects of heat during the differential shrinkage process on the bulkiness of a structured material in accordance with one embodiment of this invention.
Figure 4:
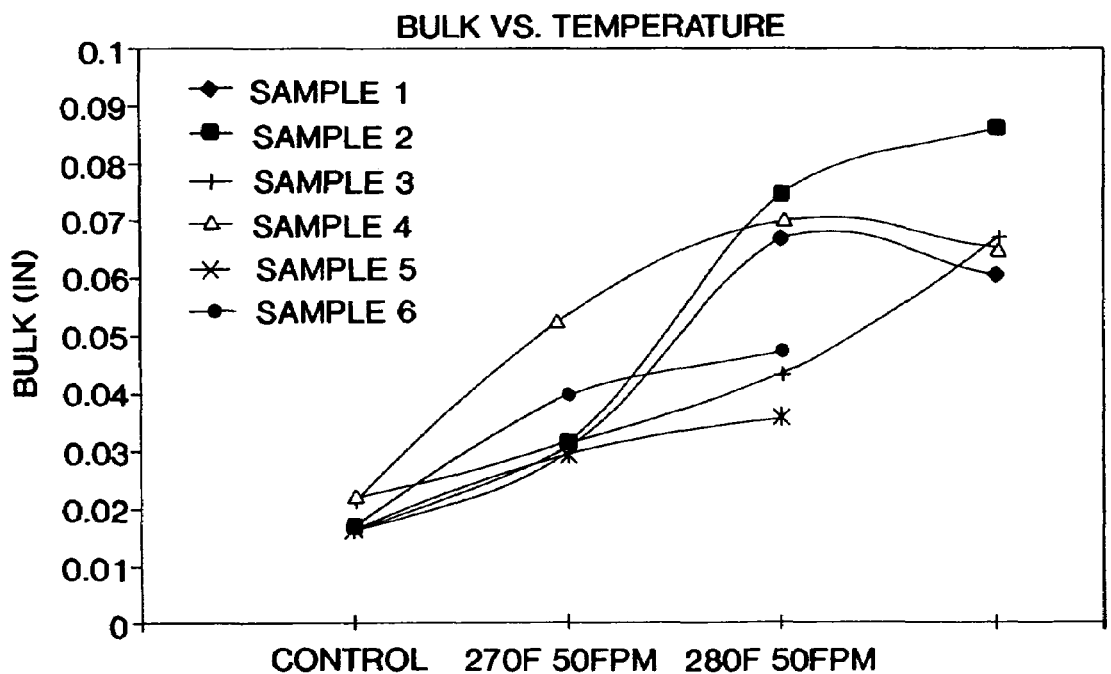
FIG. 4 shows the effects of heat during the differential shrinkage process on the bulkiness of a structured material in accordance with one embodiment of this invention.

FIGS. 3 and 4 show the heat effects on bulk for six sample structured composite materials produced according to this invention. Sample 1 is a bilayer spunbond web having the first layer 20 made of a polypropylene polymer with a Kaolin filler added and the second layer 30 made of an ethylene-propylene random copolymer (3% by weight ethylene and 97% by weight propylene). Kaolin is a clay filler made by ECC located in Roswell, Ga. Sample 2 is a bilayer spunbond web having the first layer 20 made of a polypropylene polymer and the second layer 30 made of an ethylene-propylene random copolymer (3% by weight ethylene and 97% by weight propylene). Sample 3 is a bilayer spunbond web having the first layer 20 made of a polypropylene polymer with a Kaolin filler added and the second layer 30 made of an ethylene-propylene random copolymer (3% by weight ethylene and 97% by weight propylene). The polypropylene polymer blend was extruded at 0.8 grams per hole per minute (ghm) and the ethylene-propylene copolymer was extruded at 0.5 ghm. Sample 4 is a bilayer spunbond web having the first layer 20 made of a polypropylene polymer with a Kaolin filler added and the second layer 30 made of an ethylene-propylene random copolymer (3% by weight ethylene and 97% by weight propylene). The polypropylene polymer blend was extruded at 0.5 ghm and the ethylene-propylene copolymer was extruded at 0.8 ghm. Sample 5 is a bilayer spunbond web having the first layer 20 and the second layer 30 made of a pink ethylene-propylene random copolymer (3% by weight ethylene and 97% by weight propylene). Sample 6 is a bilayer spunbond web having the first layer 20 and the second layer 30 made of a white ethylene-propylene random copolymer (3% by weight ethylene and 97% by weight propylene).

As shown in FIGS. 3 and 4, the bulk and structure 40 of the structured composite material 10 generally increased as the temperature applied to the composite material during the differential shrinkage process increased. Further, the rate at which the composite material moves through the cure oven may effect the overall bulk and structure 40 of the structured composite material 10. The increased bulk and structure 40 are a direct result of the differential shrinkage of the second layer 30, which causes the first layer 20 to bunch or pucker to produce the structure 40 of the structured composite material 10.

Figure 5:
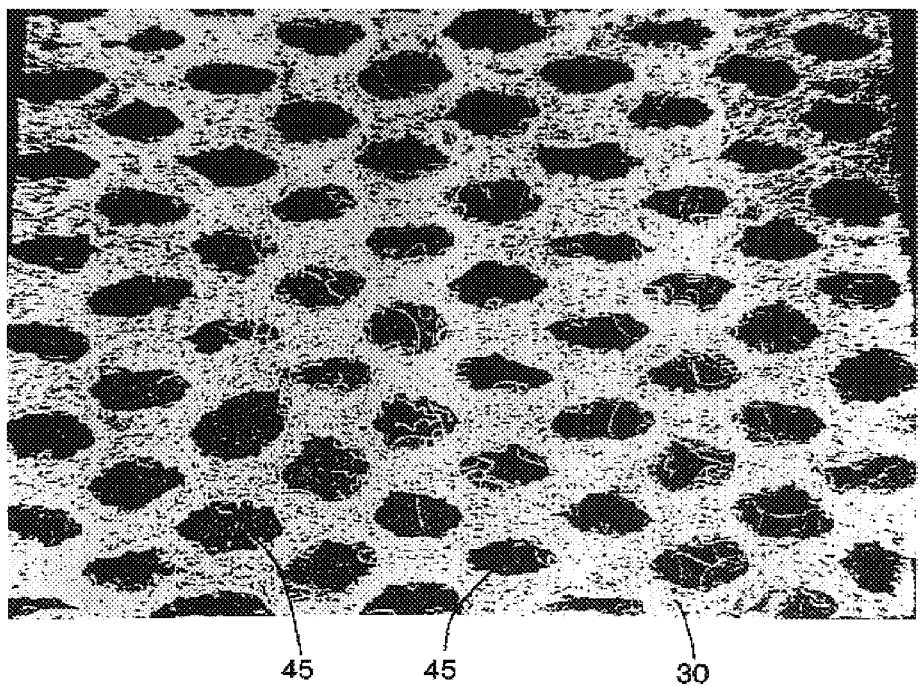
FIG. 5 is a photograph of a second layer having apertures, formed during a differential shrinkage process in accordance with one embodiment of this invention.

In accordance with one embodiment of this invention, the second layer 30 is slit apertured to form a plurality of the apertures 45 in the second layer 30, as shown in FIG. 5. Upon heating of the composite material, the slit apertured second layer 30, desirably a film or a meltspun fabric, shrinks, causing the first layer 20 to pucker, thus forming the structure 40. As the second layer 30 shrinks, the slits 44 (or similar openings) open to form a plurality of uniformly-shaped apertures 45 without any mechanical stretching. Desirably, the uniformly-shaped apertures 45 are generally circular. The apertures 45 may have a non-circular shape, for example the apertures may be elliptical, rectangular or any other suitable shape. The apertures 45 remain open after the differential shrinkage of layers 20, 30. The structured composite material 10 surrounding and/or forming the apertures 45 exhibits an increased bulk and structure 40 as a result of the shrinkage.

Figure 6:
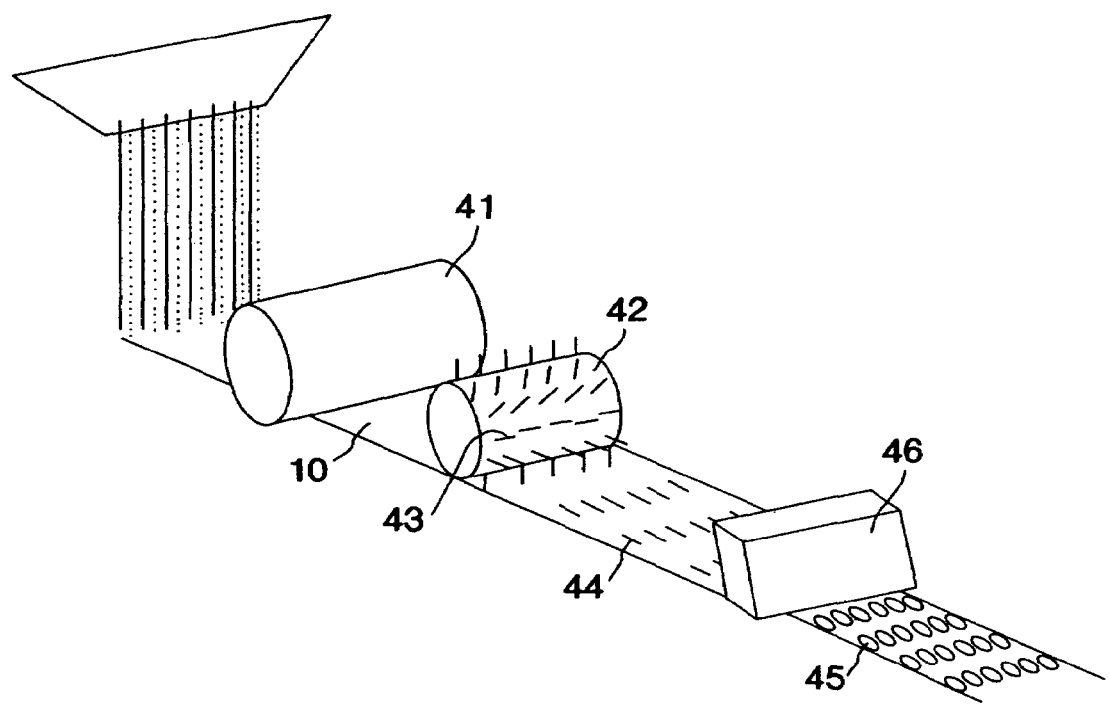
FIG. 6 is an apparatus for forming slits and corresponding apertures in a continuous in-line process in accordance with one embodiment of this invention.

Referring to FIG. 6, after the second layer 30 is bonded to the first layer 20, for example using a conventional bond roll 41, the composite material is passed through a slitting device 42 having a plurality of slitting knives 43. The slitting knives 43 cut or form slits 44 in the second layer 30. The slitting knives 43 may also cut or form slits 44 in the first layer 20. A corresponding anvil roll (not shown) may be positioned on the other side of the composite material to form a nip which applies pressure to the composite material as it travels through the nip. The anvil roll may be made of or coated with a rubber material or other suitable material so as not to dull and/or damage the slitting knives 43.

Alternatively, expanded metal plates may create the slits 44 in the second layer 30. The slits 44 can be placed in the second layer 30 in a machine direction, in a cross machine direction and/or in an angular direction so that the slits 44 cover both the machine direction and the cross machine direction. The orientation of the slits 44 is important for optimal fluid absorption and for extensibility of the structured composite material 10 in desired directions. The slits 44 can also be created in the first layer 20, if desired.

The composite material passes through a heat supply 46, desirably in-line with the slitting device 42, wherein the composite material is heated. The composite material may be heated using any means known to one having ordinary skill in the art. The second layer 30 shrinks relative to the first layer 20 to form the structure 40 of the structured composite material 10. As the structure 40 is formed, each slit 44 expands or opens to form a corresponding aperture 45. The slits 44 formed as the composite material passes through the slitting device 42 provide sufficient adhesion between the second layer 30 and the first layer 20 so that the slits 44 open cleanly to form the apertures 45 when the composite material is heated.

The slit 44 and subsequent aperture 45 size are a function of the size of the slitting knives 43, the polymer distribution, the polymer composition, and the amount of heat applied to the material by the heating supply 46. The length and orientation of the slits 44 may vary. The slits 44 should be long enough to create the apertures 45 having the desired diameter of about 100 microns to about 10,000 microns (sufficient to transfer particles of similar or smaller diameter) after the shrinkage of the second layer 30 occurs.

In embodiments wherein the apertures 45 are not circular, a distance from one point on a perimeter of the aperture 45 to an opposite point on the perimeter, along an axis, desirably has a length of about 100 microns to about 10,000 microns. For example, a generally elliptical aperture 45 will have a distance from one point on the perimeter of the ellipse to an opposite point on the perimeter of the ellipse along the minor axis of about 100 microns to about 10,000 microns. Similarly, a generally rectangular aperture 45 has a distance from a first side to an opposite second side, along the shorter axis of the rectangle, of about 100 microns to about 10,000 microns.

Alternatively, the apertures 45 may also be formed with a roller or a wire having a plurality of protrusions. The roller or the wire may be added to the continuous in-line process or it can be added, for example, to a pad or a diaper line so that the second layer 30 can be apertured during the product making process. As the composite material passes through a confined space defined by a nip formed between the roller and a smooth roller or a surface, the plurality of protrusions form apertures 45 in the second layer 30.

In accordance with one embodiment of this invention, an apertured structured heterogenous material 10 is produced from a heterogeneous mixture of homogeneous fiber sets. Desirably, each homogeneous component or set of fibers is composed of a different polymer, having a different shrinking point and a unique shrinkage extent. Alternatively, the first and second homogeneous components may be the same or similar polymer with different characteristics and/or properties. In accordance with one embodiment of this invention, the heterogeneous material is produced having a first homogeneous component having a first shrinkage extent and a second homogeneous component having a second shrinkage extent different from the first shrinkage extent. Suitable polymers and polymer blends used to produce the components of the structured heterogenous material 10 include those used to produce the first layer 20 and/or the second layer 30 of the structured composite material 10. The polymers can be chosen to exploit the differential shrinkage anticipated by the polymer properties. The heterogeneous material changes in density and porosity in response to the temperature profile during differential shrinkage. Differential shrinkage of the different fiber sets provides an increase in overall pore radius and pore volume to the structured heterogenous material 10, increasing the bulk and structure 40 and lowering the overall density of the structured heterogenous material 10.

For example, a polyethylene-alpha olefin copolymer and a polypropylene can be melt spun to form the heterogeneous material having fibers of distinct polymer composition with an initial basis weight of about 0.2 osy to about 2.0 osy, more desirably about 0.3 osy to about 1.5 osy, still more desirably about 0.7 osy. Other suitable polymer combinations include, but are not limited to, other thermoplastic polymers with different shrinkage extents, for example polyesters, polyamides, other olefinic copolymers, biconstituents and blends thereof. Desirably, the heterogenous material has a bond area of about 1.0% to about 8.0%, more desirably about 5.0% to minimize land area and maximize fiber area.

A filler, for example calcium carbonate, diatomaceous earth, titanium dioxide, talc, or the like, may be added to at least one of the homogeneous components, for example the polypropylene polymer fibers to impart an aesthetically pleasing hand to the heterogeneous material. The filler enhances the heat absorption properties of the polymers and thus increases the options for thermal initiation of shrinkage.

Heat is subsequently introduced to the heterogeneous material to produce the structure 40 of the heterogenous material. The polyethylene copolymer fibers shrink at a lower shrinking temperature than the polypropylene polymer fibers. In accordance with one embodiment of this invention, heat is introduced at a temperature sufficient to shrink the polyethylene copolymer fibers but not the polypropylene polymer fibers. Alternatively, heat may be introduced to the heterogeneous material at a temperature sufficient to shrink the polyethylene copolymer fibers and the polypropylene polymer fibers, whereby the polyethylene copolymer fibers shrink to a greater extent than the polypropylene polymer fibers. Heat is introduced to the heterogeneous material by conventional means including, but not limited to, a hot air gun, a cure oven, a convection oven, an infrared-heater, microwave, radio frequency and a through-air bonder. For example, the first layer 20 may be passed through a cure oven set at about 250° F. to about 300° F., desirably about 270° F. to about 290° F. at a rate of about 25 feet per minute (fpm) to about 300 fpm, desirably about 50 fpm to about 250 fpm. The heat introduced to the heterogeneous material as it passes through the cure oven and at least the polyethylene copolymer fibers shrink.

As a result of the polyethylene copolymer fiber shrinkage, the polypropylene fibers pucker to produce the structure 40 of the structured heterogenous material 10. Desirably, the heterogeneous material shrinks to about 0% to about 99% of its initial length, more desirably to about 10% to about 70% of its initial length to produce a soft, structured heterogenous material 10. Further, the heterogeneous material may be slit apertured before applying heat to provide a plurality of generally uniformly-shaped apertures 45 during the differential shrinkage process, as discussed above.

Experiments were run in which the heterogeneous material contained 38–50% by weight polypropylene fibers and 50–62% by weight fibers formed from an ethylene-propylene copolymer containing 3% by weight ethylene and 97% by weight propylene. As shown in Table 1, the introduction of heat to the heterogeneous material resulted in an increased basis weight and bulk, as well as an increase in the average permeability of the structured heterogeneous material 10. Further, the introduction of heat to the heterogeneous material results in a change in density of about 53%. As suggested in Table 1, the density of the structured heterogenous material 10 can be lowered significantly, depending on the change in thickness of the structured heterogeneous material 10. The reduction in density may be about 0% to about 95%, desirably about 40% to about 70%. In another embodiment of this invention, the density of the structured heterogenous material 10 may increase as a result of differential shrinkage. An outer layer or topsheet, for example a film liner of a meltspun fabric, may be applied and/or bonded to the heterogeneous material before or after heating the heterogeneous material. Desirably, the topsheet has a shrinkage extent different from the first shrinkage extent and the second shrinkage extent.

TABLE 1

| Polymer Conditions | Polypropylene/ Copolymer as spun | Polypropylene/Copolymer treated at 275° F., 70 fpm |
| --- | --- | --- |
| Basis weight (g/m$^2$) | 25 | 31 |
| Basis weight (osy) | 0.73 | 0.92 |
| Bulk (m) | 0.00044 | 0.0012 |
| Density (Basis weight/Bulk: g/m$^3$) | $5.6 \times 10^4$ | $2.6 \times 10^4$ |

TABLE 1-continued

| Polymer Conditions | Polypropylene/ Copolymer as spun | Polypropylene/Copolymer treated at 275° F., 70 fpm |
|---|---|---|
| Change in Density (%) | — | 53 |
| Average Permeability (Darcies) | 1350 | 2610 |

TEST METHODS

A. Rate Block Intake Test

Figure 7:
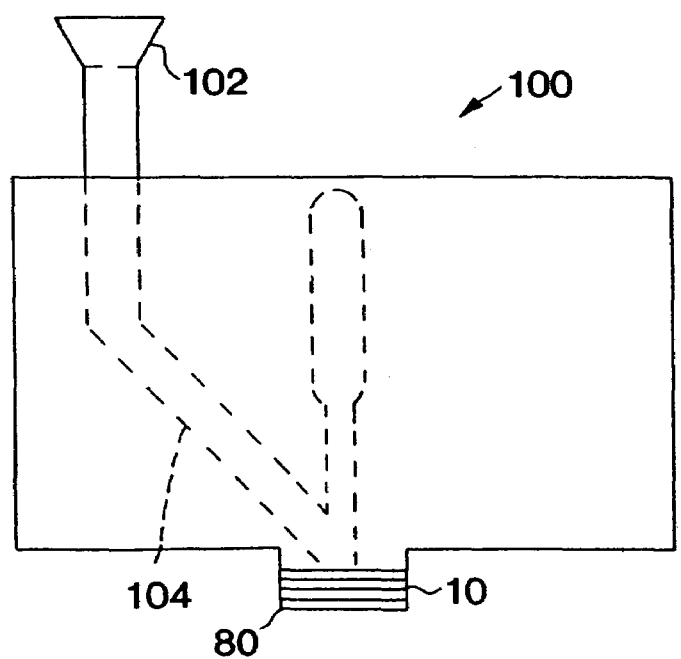
FIG. 7 is a schematic diagram of a rate block apparatus suitable for use in determining fluid intake time of a material or material system.

This test is used to determine the intake time of a known quantity of fluid into a material and/or material system. As shown in FIG. 7, the test apparatus consists of a rate block 100. A 4"×4" piece of absorbent 80 and structured material 10 are die cut. The specific structured materials 10 are described in the specific examples. The absorbent 80 used for these studies was standard and consisted of a 250 g/m² airlaid made of 90% Coosa 0054 and 10% HC T-255 binder. The total density for this system was 0.10 g/cc. The structured material 10 was placed over the absorbent 80 and the rate block 100 was placed on top of the two materials. 2 mL of a menses simulant was delivered into the test apparatus funnel 102 and a timer started. The fluid moved from the funnel 102 into a capillary 104 where it was delivered to the structured material 10 or material system. The timer was stopped when all the fluid was absorbed into the structured material 10 or material system as observed from the chamber in the test apparatus. The intake time for a known quantity of test fluid was recorded for a given structured material 10 or material system. This value is a measure of the structured material 10 or material system's absorbency. Typically, 5 to 10 repetitions of this test were performed and average intake time was determined.

B. Rewet Test

This test is used to determine the amount of fluid that will come back to the surface when a load is applied. The amount of fluid that comes back through the surface is called the "rewet" value. The more fluid that comes to the surface, the larger the "rewet" value. Lower rewet values are associated with a dryer material and hence a dryer product. In considering rewet, three properties are important: (1) intake, if the material/system does not have good intake then fluid can rewet, (2) ability of absorbent to hold fluid (the more the absorbent holds onto the fluid the less is available for rewet), and (3) flowback, the more the structured material prohibits fluid from coming back through the structured material, the lower the rewet.

A 4"×4" piece of absorbent and structured material 10 were die cut. The specific structured materials 10 are described in the specific examples. The absorbent used for these studies was standard and consisted of a 250 g/m² airlaid made of 90% Coosa 0054 and 10% HC T-255 binder. The total density for this system was 0.10 g/cc. The structured material 10 was placed over the absorbent and the rate block was placed on top of the two materials. In this test, 2 mL of menses simulant are insulted into the rate block apparatus and allowed to absorb into a 4"×4" sample of the structured material 10 which is placed on top of the 4"×4" absorbent. The fluid is allowed to interact with the system for 1 minute and the rate block rests on top of the materials. The material system, structured material 10 and absorbent are placed onto a bag filled with fluid. A piece of blotter paper is weighed and placed on top of the material system. The bag is traversed vertically until it comes into contact with an acrylic plate above it, thus pressing the whole material system against the plate blotter paper side first. The system is pressed against the acrylic plate until a total of 1 psi is applied. The pressure is held fixed for 3 minutes after which the pressure is removed and the blotter paper is weighed. The blotter paper retains any fluid that was transferred to it from the material system. The difference in weight between the original blotter and the blotter after the experiment is known as the "rewet" value. Typically, 5 to 10 repetitions of this test were performed and average rewet was determined.

C. Pore Size Measurements

The pore radius distribution chart (FIG. 2) shows pore radius in microns in the x-axis and pore volume (volume absorbed in cc of liquid/gram of dry sample at that pore interval) in the y-axis. This is determined by using an apparatus based on the porous plate method first reported by Burgeni and Kapur in the *Textile Research Journal*, Volume 37, pp. 356–366 (1967). The system is a modified version of the porous plate method and consists of a movable Velmex stage interfaced with a programmable stepper motor and an electronic balance controlled by a computer. A control program automatically moves the stage to the desired height, collects data at a specified sampling rate until equilibrium is reached, and then moves to the next calculated height. Controllable parameters of the method include sampling rates, criteria for equilibrium and the number of absorption/desorption cycles.

Data for this analysis were collected using mineral oil in desorption mode. That is, the material was saturated at zero height and the porous plate (and the effective capillary tension on the sample) was progressively raised in discrete steps corresponding to the desired capillary radius. The amount of liquid pulled out from the sample was monitored. Readings at each height were taken every fifteen seconds and equilibrium was assumed to be reached when the average change of four consecutive readings was less than 0.005 g. This method is described in more detail in U.S. Pat. No. 5,679,042 by Eugenio Go Varona, incorporated in its entirety herein by reference.

As shown in FIG. 2, samples 2a through 2d each were a bilayer spunbond web having a layer made of a polypropylene polymer with a Kaolin filler and a layer made of an ethylene-propylene random copolymer (3% by weight ethylene and 97% by weight propylene). Sample 2a was a control. Sample 2b was passed through a cure oven at a temperature of about 280° F. at a rate of about 250 feet per minute (fpm). Sample 2c was passed through the cure oven at a temperature of about 270° F. at a rate of about 70 fpm. Sample 2d was passed through the cure oven at a temperature of about 280° F. at a rate of about 70 fpm.

D. Basis Weight

The basis weight of a structured material is determined by measuring the mass of a structured material sample, and dividing it by the area covered by the sample.

E. Air Permeability Test

This test determines the airflow rate through a specimen for a set area size and pressure. The higher the airflow rate per a given area and pressure, the more open the material is, thus allowing more fluid to pass therethrough. Air permeability was determined using a pressure of 125 Pa (0.5 inch water column) and was reported in cubic feet per minute per square foot. The air permeability data reported herein can be obtained using a TEXTEST FX 3300 air permeability tester.

F. Tensile Test

This test measures the strip tensile/energy and elongation of a specimen. Samples are measured in the machine direction (MD) and the cross direction (CD). A sample of 3 inches×6 inches is placed on the pneumatic jaws of an Instron tensile tester with a load cell of 10 pounds, setting up the gage length to 3 inches and a crosshead speed of 12 inches/minute. The sample is placed on the clamps and the equipment is started. The top clamp is lifted by the equipment at the cross head speed until the specimen breaks. The strip tensile peak load (pounds), the maximum load before the specimen ruptures, and the elongation at break (%) (peak strain) are read from the instrument. The modulus is calculated in the typical manner as the slope of the best fitting line on a stress/strain curve as calculated from zero to the proportional limit. The energy is calculated with the following formula:

$$E = R/500 \times L \times S; \qquad \text{Eq. (2)}$$

where

E=Energy (inch per pound)
R=Integrator reading
L=Full scale load in pounds
S=Crosshead speed (inch/minute)

This is performed at a constant temperature of 73+/−2 F and a relative humidity of 50+/−2%.

G. Peel

This method describes a protocol to measure the necessary force to pull apart two layers of a composite material.

A sample of 6 inches (machine direction)×2 inches is cut on a precision paper cutter. A tensile strength equipment such as an Instron model 1000, 1122 or 113 or a Thwing Albert model Intelect II is used to measure force. The equipment must have clamps that measure 1 inch parallel to the direction of load and 3 inches perpendicular direction. The gauge length must be set to 1 inch and the cross head speed to 12 inches/minute. Samples are measured in the machine direction (MD) and the cross direction (CD). The sample is prepared by separating apart from the composite material the second layer (about 2 inches) and both materials are clamped to each jaw of the equipment. After starting the equipment, the jaws separate and the load versus distance of separation is recorded. The peak peel load (lbs) is the largest load over a distance of separation from 1 to 7 inches. The average peel load is the average load over a distance of separation from 1 to 7 inches. The testing is performed at a constant temperature of 73+/−F and a relative humidity of 50+/−2%.

EXAMPLE 1

Several structured composite materials 10 were produced in accordance with the process of this invention and evaluated to compare the properties of each material with those of conventional model cover materials. A 100 gsm $CaCO_3$ filled linear low density polyethylene (LLDPE) film, made using 45% by weight of m-LLDPE and 55% by weight $CaCO_3$, is oriented in the machine direction using a machine direction orientor to three times its original length and then bonded to a nonwoven surge material. The bond pattern used was a S-weave bond pattern. The film layer of the composite material has a low shrinking temperature and is apertured during the bonding process by burning off the polymers in the bond areas. As the apertured composite material is heated, the film layer shrinks, thus producing the structure 40 of the apertured structured composite material 10.

During the bonding process, the film layer was positioned against the pattern roll and the nonwoven surge material was positioned against the anvil roll. This reversed heating approach was used due to the higher shrinking polymer of the nonwoven surge material. The nonwoven surge material fibers where heated to a higher temperature while the film layer remained relatively cooler. Using this approach, the $CaCO_3$ filled LLDPE film was thermally bonded to the nonwoven surge material. Additionally, when the film layer was positioned against the pattern roll during the bonding process, a better topography was created having a more three-dimensional film side aperture as compared to positioning the film layer on the anvil roll.

The film materials used in this example consisted of: (1) XSF 622 film made of 55% $CaCO_3$ and 45% metallocene-catalyzed mLLDPE (100% Dow Engage 8200); (2) XSF 623 film made of 55% $CaCO_3$ and 45% mLLDPE (75% Dow Engage 8200 and 25% Dow Affinity PL1845); and (3) film made of polyethylene available from Pliant Corporation located in Salt Lake City, Utah, U.S.A. The Engage 8200 material and the Affinity PL1845 material are available from the Dow Chemical Company located in Midland, Mich., U.S.A.

The nonwoven surge materials used in this example consisted of: (1) through-air-bonded ("TABed") side-by-side bicomponent polypropylene/polyethylene (hollow fiber) with no treatment prior to bonding; (2) point bonded polypropylene ("PP") spunbond ("SB") with 0.3% Ahcovel Base N-62 surfactant; and (3) through-air-bonded side-by-side bicomponent ("TABBI") polypropylene/polyethylene staple fiber treated with HR6 surfactant by Chisso Corporation, Osaka, Japan. The composite cover material samples made with surge materials (1) and (2) were treated with 2:1 ratio of Ahcovel Base N-62/Masil SF-19 surfactant combination at a 2% add-on level. Ahcovel Base N-62 is made by Unigema Inc., a division of ICI of New Castle, Del. Masil SF-19 is available from BASF in Gurnee, Ill. The composite cover material sample made with the TABBI surge material was not treated. All samples were measured with an airlaid absorbent core at 250 gsm. Tables 2 and 3 show the results of the tests.

Figure 8:
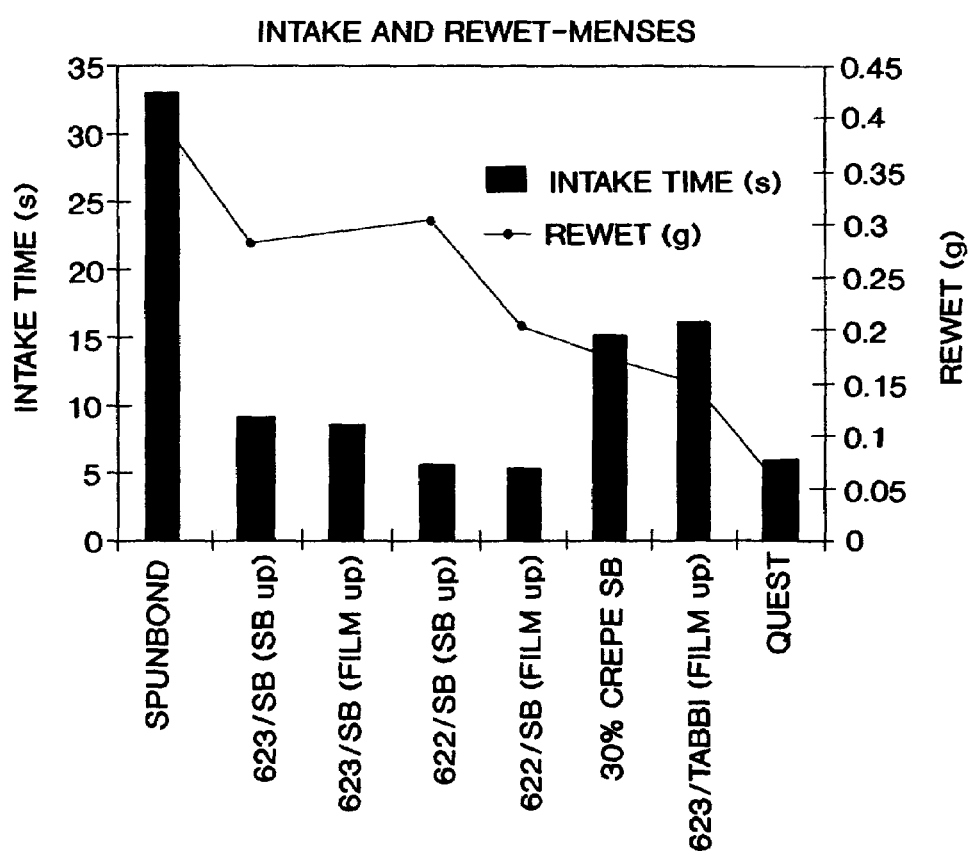
FIG. 8 is chart comparing the intake time and rewet value of a structured material produced in accordance with one embodiment of this invention with the intake time and rewet value of conventional cover materials.

As shown in Tables 2 and 3, as well as in FIG. 8, the composite material 10 of this invention is favorably comparable to the more expensive model cover materials. In general, the rewet values are better when the film layer is facing the user rather than the nonwoven surge material facing the user.

TABLE 2

Intake and Rewet Test Results

| Film Code | Nonwoven Surge Material | Composite Basis Weight (osy) | Side Facing User | Intake Time (sec) | Rewet Value (gms) | Treatment |
|---|---|---|---|---|---|---|
| XSF 623 | 0.4 osy SB, wire weave | 1.95 | SB | 9.1 | 0.28 | 2:1 Ahcovel/SF-19 at 2% add-on |
| XSF 623 | 0.4 osy SB, wire weave | 1.95 | Film | 8.4 | 0.29 | 2:1 Ahcovel/SF-19 at 2% add-on |
| XSF 622 | 0.4 osy SB, wire weave | 1.67 | SB | 9.5 | 0.44 | 2:1 Ahcovel/SF-19 at 2% add-on |

TABLE 2-continued

Intake and Rewet Test Results

| Film Code | Nonwoven Surge Material | Composite Basis Weight (osy) | Side Facing User | Intake Time (sec) | Rewet Value (gms) | Treatment |
|---|---|---|---|---|---|---|
| XSF 622 | 0.4 osy SB, wire weave | 1.67 | Film | 7.7 | 0.39 | 2:1 Ahcovel/ SF-19 at 2% add-on |
| XSF 622 | 0.7 osy, bicomponent hollow fiber, denier of 3.5 | 2.90 | SB | 5.4 | 0.3 | 2:1 Ahcovel/ SF-19 at 2% add-on |
| XSF 622 | 0.7 osy, bicomponent hollow fiber, denier of 3.5 | 2.90 | Film | 5.1 | 0.2 | 2:1 Ahcovel/ SF-19 at 2% add-on |
| XSF 623 | 0.7 osy TABBI | 2.12 | Film | 12–15.8 | 0.04–0.24 | Bonded Carded Web (BCW) treated by manuf. |
| QUEST | 0.7 osy TABBI | 1.32 | Film | 6–10 | 0.05 | BCW treated by manuf. |
| None | SB | 0.40 | SB | 33 | 0.4 | 0.3% Ahcovel |
| None | 30% creped SB | 0.52 | SB | 15 | 0.17 | 0.3% Ahcovel |

TABLE 3

Tensile Properties

| Film Code | Nonwoven Surge Material | Basis Weight (osy) | Basis Weight (gsm) | MD Peak Tensile Load (gms) | MD Peak Strain (%) | CD Peak Tensile Load (gms) | CD Peak Strain (%) | MD Peel (gms) |
|---|---|---|---|---|---|---|---|---|
| XSF 623 | 0.7 osy TABBI | 2.1 | 70 | 5094 | 17 | 1107 | 66 | 217 |
| XSF 622 | 0.4 osy PP SB | 1.1 | 36 | 3237 | 18 | 1430 | 38 | 233 |
| XSF 622 | 3.5 dfp hollow PP/PE fiber TABed | 1.6 | 55 | 2384 | 31 | 1084 | 53 | 135 |
| XSF 623 | 0.4 osy PP SB | 1.6 | 53.8 | 3719.5 | 24 | 1859.8 | 48.6 | 154.9 |
| Pliant LDPE film | 0.7 osy TABBI | 1.6 | 53.7 | 6305 | 19 | — | — | 128.6 |

Figure 9:
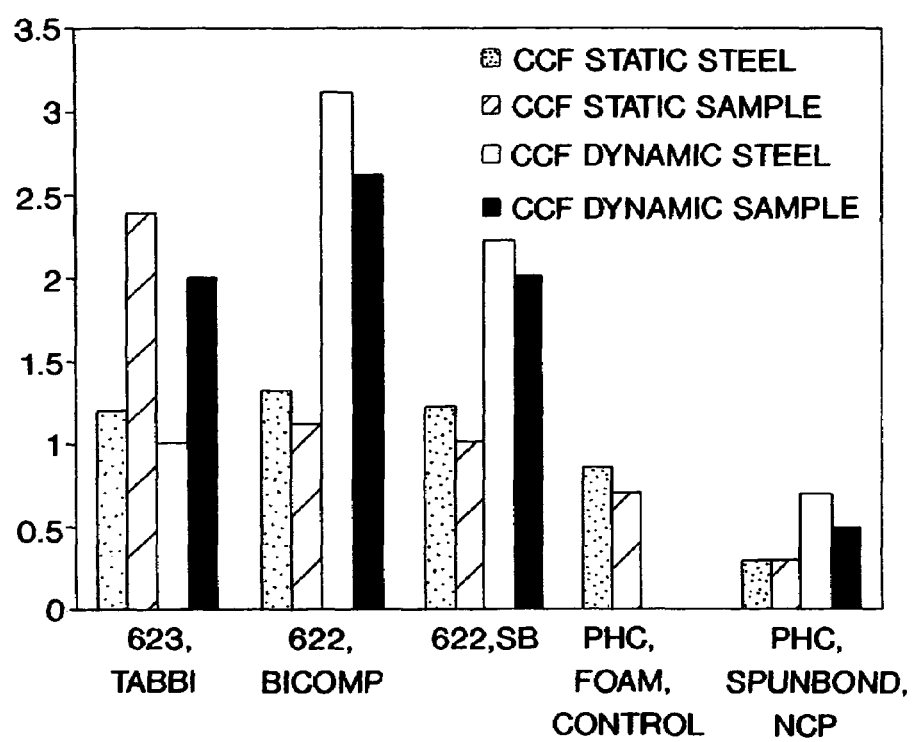
FIG. 9 is chart comparing the coefficient of friction values of structured materials produced in accordance with one embodiment of this invention with the coefficient of friction values of conventional cover materials.

Referring to FIG. 9, the results of a coefficient of friction test against steel indicated that the structured composite material 10 of this invention has frictional properties equivalent to or higher than the frictional properties of conventional cover materials, while improving intake and rewet values. Such high friction surfaces are ideal for applications such as fenestration products.

EXAMPLE 2

Several samples of structured composite materials 10 were produced according to this invention having a first layer 20 made of a polypropylene polymer and a slit apertured second layer 30 made of an ethylene-propylene copolymer 30. Sample 1 was made with a non-shrinking first layer 20 and a slit apertured second layer 30 having slits 44 with a machine direction orientation. Sample 2 was made with a non-shrinking first layer 20 and a slit apertured second layer 30 having slits 44 with a diagonal orientation. Sample 3 was a composite cover material having a first layer 20 of polypropylene polymer and a second layer 30 of ethylene-polypropylene copolymer. The polypropylene polymer was made by the Exxon Mobil Chemical Company under the trade designation Exxon 3155 and the copolymer was made by Union Carbide under the trade designation 6D43. Each sample was treated with 0.3% Ahcovel surfactant add-on and tested for menses and rewet performance. The control code for the test was a standard polypropylene pad wrap produced commercially from Berkeley having a basis weight of about 0.6 osy with an EHP bond pattern and treated with 0.3% Ahcovel treatment. The five codes were treated using a bench top dip and squeeze method.

Figure 10:
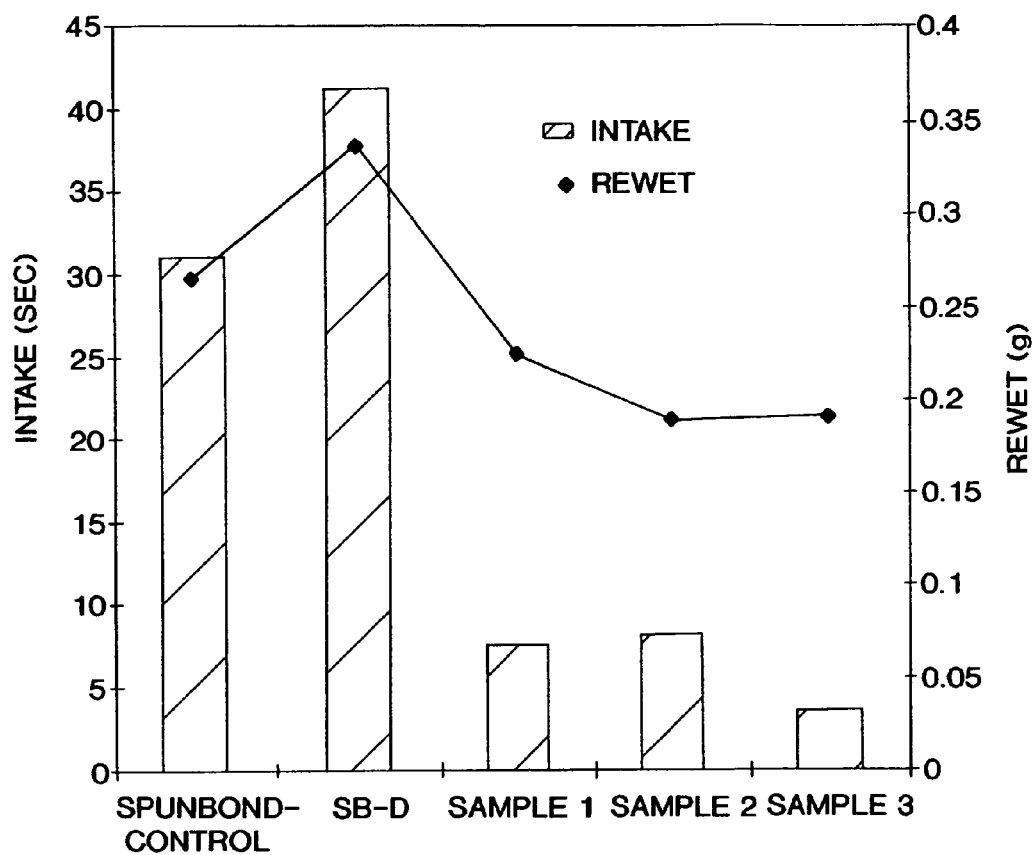
FIG. 10 is a chart comparing the intake time and rewet value of a slit apertured structured material produced in accordance with one embodiment of this invention with the intake time and rewet value of conventional cover materials.

As shown in FIG. 10, the slit apertured structured composite material 10 (Sample 1 and Sample 2) and the structured material 10 (Sample 3) produced by differential shrinkage outperforms the other codes in terms of intake rate, less than about 8.0 seconds, and rewet value, less than about 0.2 grams.

Although references made herein are directed to personal care absorbent products, it is apparent to one having ordinary skill in the art that the structured material 10 in accordance with this invention may be used for articles or products other than personal care absorbent products. Such articles or products include, but are not limited to, fabrics for conveying fluids, spacer layers, fasteners, filter medium for liquid and air filtration applications, and wipers. For example, fabrics that deliver a cream or a soap, wipers impregnated with cleaning agents, cleaning products which scrub and convey material away from the surface being cleaned, and other products that rely on porosity and topography to function. The structured material produced in accordance with this invention may also be used as a cost-effective replacement for materials such as surge materials, loop materials and outer covers.

While the invention has been described in detail with respect to specific embodiments thereof, it will be appreciated to those skilled in the art, upon attaining an understanding of the foregoing may readily conceive of alterations to, variations of and equivalents to these embodiments. Accordingly, the scope of the present invention should be assessed as that of the appended claims and any equivalents thereto.

What is claimed is:

1. A method for producing a structured composite material having a plurality of apertures for accommodation passage of fluids through the structured composite material, the method comprising the steps of:
    forming a first layer having a first shrinkage extent, said first layer comprising a fibrous thermoplastic nonwoven web;
    extruding a heat shrinkable second layer onto the first layer, the second layer comprising a thermoplastic film and having a second shrinkage extent different from the first shrinkage extent;
    forming the plurality of apertures only through the second layer after extrusion; and
    differentially heat shrinking the second layer relative to the first layer to increase a bulk of the composite material and produce the structured composite material;
    whereby the apertures are effective in transferring particles into the structured composite material and the first layer is effective in retaining them.

2. The method of claim 1, wherein the plurality of apertures are formed through the second layer using one of pin embossing, slitting, laser embossing and thermal embossing.

3. The method of claim 1, wherein the apertures formed each have a diameter of about 100 microns to about 10,000 microns.

4. The method of claim 1, wherein the first layer comprises a polypropylene polymer.

5. The method of claim 1, wherein the second layer comprises an ethylene-propylene random copolymer.

6. The method of claim 1, wherein an initial bulk of the composite material is increased by at least 50% during the shrinkage step.

7. The method of claim 1, wherein an initial bulk of the composite material is increased by at least 100% during the shrinkage step.

8. The method of claim 1, further comprising the step of heating the composite material to effect shrinkage of at least the second layer.

9. The method of claim 8, wherein the composite material is heated using one of infrared, hot air, microwave, a cure oven and a through-air-bonder.

10. The method of claim 1, wherein a filler is added to the film.

11. The method of claim 10, wherein the filler is selected from the group consisting of clay, calcium carbonate, diatomaceous earth, titanium dioxide, and talc.

12. The method of claim 1, wherein the apertures are formed by producing a plurality of slits through the second layer, and opening each slit to form a corresponding aperture.

13. The method of claim 12, wherein the slits are formed using expanded metal plates.

14. The method of claim 12, wherein the slits are formed in one of a machine direction, a cross machine direction and an angular direction.

* * * * *

UNITED STATES PATENT AND TRADEMARK OFFICE
CERTIFICATE OF CORRECTION

| | | |
|---|---|---|
| PATENT NO. | : 7,118,639 B2 | Page 1 of 1 |
| APPLICATION NO. | : 09/871171 | |
| DATED | : October 10, 2006 | |
| INVENTOR(S) | : Mary Lucille Delucia et al. | |

It is certified that error appears in the above-identified patent and that said Letters Patent is hereby corrected as shown below:

Column 21, line 6, delete "accommodation" and insert --accommodating-- in its place.

Signed and Sealed this

Twenty-sixth Day of December, 2006

JON W. DUDAS
*Director of the United States Patent and Trademark Office*